Oct. 7, 1969 D. L. ARMSTRONG Plant Pat. 2,930
PEACH TREE
Filed Feb. 29, 1968
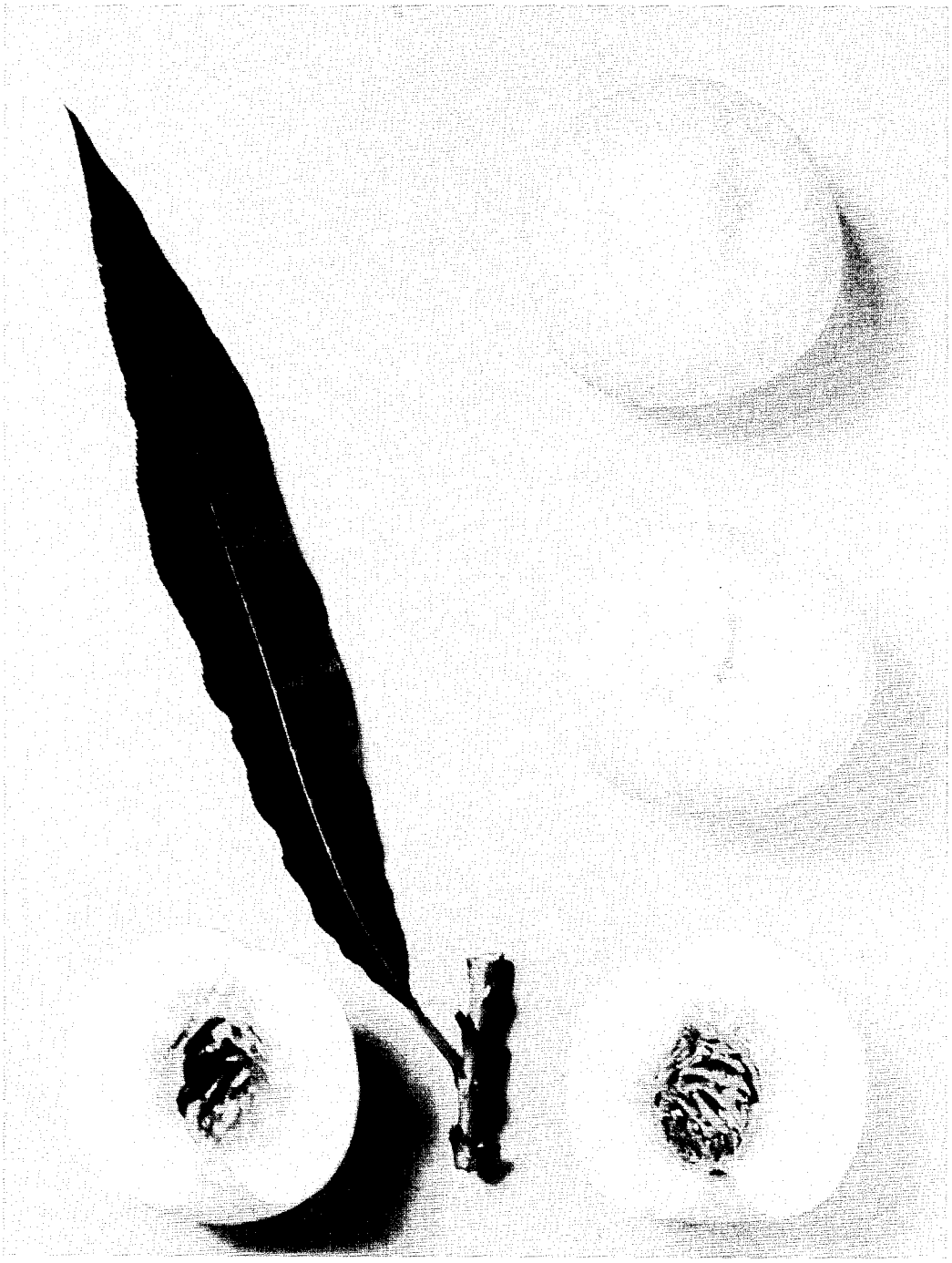
Inventor.
D. L. Armstrong
By: Robb & Robb
Attorneys.

United States Patent Office

Plant Pat. 2,930
Patented Oct. 7, 1969

2,930
PEACH TREE

David L. Armstrong, Ontario, Calif., assignor to Armstrong Nurseries, Inc., Ontario, Calif., a corporation of California Filed Feb. 29, 1968, Ser. No. 709,504
Int. Cl. A01h 5/08
U.S. Cl. Plt.—43 1 Claim The present invention relates to a new and distinct variety of dwarf peach tree of the yellow-fleshed, freestone, fruit-bearing type, which was originated by me as an open-pollinated seedling derived from open-pollination of an unnamed and unpatented, tall peach variety and which was the result of crossing an unnamed and unpatented, tall peach variety, used as the seed parent, × the peach variety known as "Springtime" (Plant Patent No. 1,268), used as the pollen parent.

The new variety is one which resulted from an extensive breeding program conducted by me with the objective of producing improved, yellow-fleshed, freestone peach varieties having a dwarf tree habit and bearing fruit which ripens in various seasons. This objective was fully achieved in the new variety, along with other desirable features, as evidenced by the following unique combination of characteristics which are outstanding in the new variety and which distinguish it from its parent, as well as from all other peach varieties of which I am aware:

(1) A vigorous, compact, bushy, dwarf tree habit, with stem internodes averaging approximately ¼ inch in length, and having leaves of relatively normal or larger size and appearance for peach and nectarine varieties, and giving the tree an attractive, densely foliaged appearance, while attaining a height of about five to six feet in about ten years with little or no pruning;

(2) Showy, pale to light pink, single flowers;

(3) A moderate chilling requirement falling between that of "Springtime" peach (Plant Patent No. 1,268) and "Tejon" peach (unpatented);

(4) Heavy fruit crop production in California;

(5) Medium sized, nearly round to somewhat laterally compressed, yellow-fleshed, freestone fruit of good quality and flavor, with moderate amount of red color in the flesh near the pit cavity;

(6) A moderate amount of pubescence on the skin of the fruit;

(7) An attractive skin color ranging from near Canary Yellow to near Buttercup Yellow, all lightly overlaid with a moderate amount of near Delft Rose to Rose Opal, with the amount of red color being only slight where fully covered by dense foliage during ripening, but increasing to over fifty percent red color where more fully exposed to light; and (8) A fruit ripening period generally occurring in late July to early August at Wasco, Calif., and usually ripening from a few days to a week or ten days ahead of "Elberta" peach (unpatented).

The unnamed seed parent of the new variety was a tall peach variety having a relatively low chilling requirement and which bore yellow-fleshed, freestone fruit which ripened in the medium early season, with the fruit being of medium size, nearly round, moderately red colored and having good quality and flavor. In comparison with this parent, the new variety primarily differs therefrom by having a dwarf tree habit, and the fruit of the new variety ripens several weeks later than the fruit of this parent.

As compared with the ancestors of this seed parent, which were "Flamingo" peach (Plant Patent No. 661), "Babcock" peach (unpatented), "Double Pink" peach (unpatented), "Rio Oso Gem" peach (Plant Patent No. 84) and "Chinese Dwarf" peach (unpatented—identified as PI No. 41,395), the new variety differs from "Flamingo" peach primarily by having a dwarf instead of a tall tree habit, and the fruit of the new variety ripens several weeks earlier; the new variety differs primarily from "Babcock" peach by having a dwarf tree habit instead of the tall habit of "Babcock" peach, and the fruit of the new variety is yellow-fleshed instead of white-fleshed and ripens several weeks later; the new variety differs from "Double Pink" peach by having a dwarf instead of a tall tree habit, with single instead of double flowers, and the fruit ripens considerably earlier and has good quality as compared to the very low quality fruit which is typical of flowering peaches such as "Double Pink"; the new variety primarily differs from "Rio Oso Gem" peach by having a dwarf instead of a tall tree habit, with a lower chilling requirement, and the fruit of the new variety ripens several weeks earlier; and the new variety primarily differs from "Chinese Dwarf" peach by its skin color being attractively colored yellow and some red, fruit which is yellow-fleshed, freestone and mid-season ripening compared to the pea green skin color, white flesh, clingstone and late ripening fruit of "Chinese Dwarf."

The new variety also differs from the dwarf peach variety known as "Bonanza" (Plant Patent No. 2,213) primarily by ripening of the fruit of the new variety from six to eight weeks later, a somewhat lower chilling requirement, and pale to light pink, single flowers compared to the semi-double pink flowers of "Bonanza."

Asexual reproduction of my new variety by budding, as performed by me at Wasco, Calif., shows that the foregoing characteristics and distinctions come true to form and are established and transmitted through succeeding propagations.

The accompanying drawing shows typical specimens of the foliage, stem, fruit and stone of my new variety, with both exterior and sectional views of the fruit being shown, and all of said views being depicted in color as nearly true as is reasonably possible to make the same in a color illustration of this character.

The following is a detailed description of my new variety, as based upon observations of specimens grown at Wasco, Calif., with color terminology in accordance with Robert F. Wilson's Horticultural Colour Chart (hereinafter abbreviated as (W)) and Ridgway's Color Standards and Nomenclature (hereinafter abbreviated as (R)), except where general color terms of ordinary dictionary significance are obvious:

TREE

Habit: Vigorous; upright-spreading; compact; bushy; dwarf; stem internodes average approximately ¼ inch long; leaves relatively normal or larger size and appearance for peach varieties.

Chilling requirement: About equal to that of "Tejon" peach.

Fruit production: Bears heavy fruit crops when grown in southern California.

Current growth:

*Surface texture.*—Smooth at first, with lenticels small and minute; some larger, cracked, slightly raised lenticels appear toward the base of the more vigorous shoots as they age.

*Color.*—Green or reddish on exposed surfaces at first, with lenticels appearing as small, near white dots, all becoming more brown with age.

Two-year wood:

*Surface texture.*—Somewhat bumpy and rough effect from raised nodes and buds and their closeness together on the stem; otherwise internodes generally smooth, with some slightly raised lenticels and irregular, longitudinal striations.

*Color.*—Brown, but sometimes reddish brown.

Old wood:

*Surface texture.*—With increasing diameter of the stem, the bumpiness and rough effect from the nodes and buds become less as they are covered by the growth of the stem, becoming more smooth over all with moderate number of raised lenticels and some small longitudinal fissures.

*Color.*—From grey to grayish brown or reddish brown on more exposed surfaces.

Leaves:

*Size.*—From 6 inches to 9 inches long; from 1 inch to 1⅜ inches wide.

*Shape.*—Lanceolate, with apex acuminate.

*Color (mature).*—Upper surface — near Forest Green,, Plate XVII (R). Under surface—near Chromium Green, Plate XXXII (R).

*Petiole.*—Medium length; medium thickness.

*Margin.*—Finely serrate; glandular.

*Glands.*—Mostly reniform, but few near globose, and occasionally no glands; small size; usually 2 or 3, but rarely 4 in number; usually borne on the base of the blade or just at the point of connection of the blade with the petiole.

Vegetative buds:

*Size.*—Small.

*Shape.*—Ovoid, unless compressed between flower buds.

*Scales.*—Pubescence thick; moderate length.

*Color.*—Dark brown.

FLOWERS

Dates of first and full bloom: Over a seven-year period of observation at Wasco, Calif., first bloom ranged from February 23 to March 4, and full bloom ranged from March 3 to March 10.

Dormant flower buds:

*Shape.*—Ovoid.

*Scales.*—Pubescent.

*Color.*—Dark brown, with pubescence giving a whitish effect.

*Size (when fully open).*—Showy; medium size; about 1½ inches in diameter.

*Petalage.*—Single; usually 5 petals.

*Form.*—Cupped.

*Color (open flower).*—From pale pink to light pink.

FRUIT

Ripening dates: Generally ripens late July to early August at Wasco, Calif.; over seven years of observation, first ripening ranged from July 19 to August 8; usually ripens from a few days to a week or ten days ahead of "Elberta" peach.

Maturity when described: Tree-ripe.

Size: Generally medium size.

*Axial diameter.*—From 2¼ inches to 2¾ inches.

*Transverse diameter in suture plane.*—From 2¼ inches to 2½ inches.

*Transverse diameter at right angles to suture plane.*—From 2½ inches to 2¾ inches.

Form: Somewhat variable; near globose, but usually somewhat compressed laterally toward suture.

Suture: Usually shallow; extending from base to apex; slight depression beyond pistil point.

Ventral surface: Rounded; slightly lipped throughout, with lips unequal.

Stem cavity: Somewhat rounded, but elongated in suture plane, with suture showing on one side.

*Depth.*—About ⅜ inch.

*Width.*—From ⅝ inch to ¾ inch.

Base: Rounded.

Apex: Rounded; sometimes depressed; pistil point usually very short, but often insignificant.

Stem: Medium caliper; glabrous; weak adherence to stone. Length—from about ⅜ inch to ½ inch.

Skin:

*Thickness.*—Medium.

*Texture.*—Medium.

*Tenacity to flesh.*—Free.

*Pubescence.*—Moderate amount; medium length.

*Color.*—Ground color ranges from near Canary Yellow, Plate 2/3, page 2 (W) to near Buttercup Yellow, Plate 5/3, page 5 (W), all lightly overlaid with flecks, streaks, mottling and blushes of from near Delft Rose, Plate 020/3, page 108 (W) to near Rose Opal, Plate 022/1, page 110 (W), and amount of red coloring varies from very little where completely covered with foilage, to over 50% of the skin area where well exposed to light; illustrated fruit specimens were relatively well covered by foliage.

Flesh:

*Quality.*—Medium firm; melting; fine tender fibers.

*Aroma.*—Pronounced.

*Flavor.*—Subacid; good balance between sugar and acid.

*Color.*—Between Indian Yellow, Plate 6/2, page 6 (W) and Saffron Yellow, Plate 7/1, page 7 (W), with specks and streaks of near Crimson, Plate 22/1, page 22 (W), in area near pit cavity; surface of pit cavity from near Crimson, Plate 22/1, page 22 (W), to near Rose Opal, Plate 022/1, page 110 (W).

Stone:

*Tenacity of flesh.*—Free.

*Size.*—Medium; from about 1¼ inches to 1½ inches long; from about ⅞ inch to 1⅛ inches wide; from about ⅝ inch to ¾ inch thick.

*Form.*—Ovoid.

*Base.*—Somewhat oblique.

*Hilum.*—Oval.

*Apex.*—From acute to acuminate.

*Sides.*—Slightly unequal; irregularly furrowed toward apex and sometimes near base; pitted from base to past center.

*Ventral edge.*—Medium thickness; varies with or without wing.

*Dorsal edge.*—Narrow, shallow groove from base to past center; ridges on either side interrupted.

*Color.*—Between Cacao Brown, Plate XXVIII (R) and Pecan Brown, Plate XXVIII (R).

I claim:

1. A new and distinct variey of dwarf peach tree of the yellow-fleshed, freestone, fruit-bearing type, substantially as herein shown and described, characterized particularly as to novelty by the unique combination of a vigorous, compact, bushy, dwarf tree habit, with stem internodes averaging approximately ¼ inch in length, and having leaves of relatively normal or larger size and appearance for peach and nectarine varieties, and giving the tree an attractive, densely foliaged appearance, while attaining a height of about five to six feet in about ten years with little or no pruning, showy, pale to light pink, single flowers, a moderate chilling requirement falling between that of "Springtime" peach (Plant Patent No. 1,268) and "Tejon" peach (unpatented), heavy fruit crop production in southern California, medium sized, nearly round to somewhat laterally compressed, yellow-fleshed, freestone fruit of good quality and flavor, with a moderate amount of red color in the flesh near the pit cavity, a moderate amount of pubescence on the skin of the fruit, an attractive skin color ranging from near Canary Yellow to near Buttercup Yellow, all lightly overlaid with a moderate amount of near Delft Rose to Rose Opal, with the amount of red color being only slight where fully covered by dense foliage during ripening, but increasing to over fifty percent red color where more fully exposed to light, and a fruit ripening period generally occurring in late July to early August at Wasco, Calif., and usually ripening from a few days to a week or ten days ahead of "Elberta" peach (unpatented).

No references cited.

ROBERT E. BAGWILL, Primary Examiner